United States Patent [19]

Smith, Jr.

[11] Patent Number: 4,643,722

[45] Date of Patent: Feb. 17, 1987

[54] CLOSURE SYSTEM FOR STORAGE, TRANSPORT AND DISPOSAL OF HYPODERMIC NEEDLES

[76] Inventor: William I. Smith, Jr., 1061 Lindendale Rd., Pittsburgh, Pa. 15243

[21] Appl. No.: 747,027

[22] Filed: Jun. 20, 1985

Related U.S. Application Data

[63] Continuation-in-part of Ser. No. 482,145, Apr. 5, 1983, abandoned.

[51] Int. Cl.$^4$ ............................................... A61M 5/32
[52] U.S. Cl. .................................... 604/192; 604/263; 206/365
[58] Field of Search ................ 604/192, 263; 206/349, 206/364–366

[56] References Cited

U.S. PATENT DOCUMENTS

| | | | |
|---|---|---|---|
| 2,110,123 | 3/1938 | Eisele | 206/365 |
| 2,645,339 | 7/1953 | Toy | 206/366 |
| 2,854,976 | 10/1958 | Heydrich . | |
| 2,857,912 | 10/1958 | Feinstone et al. . | |
| 2,997,043 | 8/1961 | Flynn . | |
| 3,052,241 | 9/1962 | Myerson et al. . | |
| 3,055,364 | 9/1962 | Myerson et al. . | |
| 3,537,452 | 11/1970 | Wilks . | |
| 3,865,236 | 2/1975 | Rycroft . | |
| 4,356,822 | 11/1982 | Winstead-Hall . | |
| 4,419,098 | 12/1983 | Bennett . | |
| 4,438,845 | 3/1984 | Mochow . | |
| 4,524,868 | 6/1985 | Buckley et al. | 206/364 |

FOREIGN PATENT DOCUMENTS

| | | |
|---|---|---|
| 0530857 | 7/1955 | Italy . |
| 0448389 | 3/1968 | Switzerland . |

*Primary Examiner*—C. Fred Rosenbaum
*Assistant Examiner*—Gene B. Kartchner
*Attorney, Agent, or Firm*—Arnold B. Silverman

[57] ABSTRACT

A hypodermic needle assembly adapted for covering and uncovering the needle by relative lateral movement between a closure member and the needle. The needle has an enlargement hub portion. An elongated closure is disposed in adjacent relationship with respect to the needle and has an elongated slot which permits insertion of the needle into the closure and removal of the needle therefrom. The closure may engage the needle hub for resisting undesired removal of the closure. A closure strip is displaceably secured in overlying relationship with respect to the slot so as to provide a sterile needle. Pilot means may be provided adjacent the closure slot to facilitate insertion of the needle into the slot. An indicator may be provided to facilitate determination of closure orientation.

28 Claims, 19 Drawing Figures

CLOSURE SYSTEM FOR STORAGE, TRANSPORT AND DISPOSAL OF HYPODERMIC NEEDLES

CROSS-REFERENCE TO RELATED APPLICATION

This application is a continuation-in-part of U.S. Ser. No. 482,145 filed Apr. 5, 1983, abandoned.

BACKGROUND OF THE INVENTION

1. Field of the Invention

This invention relates to hypodermic needle closure systems and, more specifically, it relates to such systems wherein means are provided to resist undesired puncture wounds.

2. Description of the Prior Art

Modern medical techniques have resulted in the desirable, extensive use of hypodermic needles to obtain blood samples, to give injections and for infusions. One of the problems which has occurred as a result of frequent use of the existing products has been undesired puncture wounds suffered by individuals employing the hypodermic needles, such as doctors, nurses and laboratory workers as well as those in charge of housekeeping. Such inadvertent punctures have necessitated treatment of injury and frequently treatment of diseases that result from the puncture wounds. Such injuries and illnesses are troublesome not only in a physical sense, but also financially as a result of the ultimate cost in terms of lost employee time, the cost of treating the injuries and the associated record keeping.

In general, existing systems provide a cap member having a closed end wall positioned over a needle which is attached to a syringe. The cap is removed and blood is drawn or the injection or infusion may be accomplished. The needle is then recapped by inserting the pointed end of the needle into the open end of the elongated cap member and the needle is disposed of. As an alternative, the needle may be disposed of by merely discarding the same without capping, with or without alteration of the hypodermic needle structure as by removing the needle portion. Rigid boxes having suitable opening for receipt of the needles have been used.

A recent study has shown that approximately 30% of the accidental puncture wounds resulting from use of hypodermic needles has been due to accidents during recapping. Another 30% was shown to have occurred as a result of exposed needles being left in dangerous positions, such as on beds or in trash containers. See also Hollenbaugh, *Hospital Employee Health*, April 1982, and McCormick et al., *American Journal of Medicine*, April 1981.

With respect to accidental needle sticks with needles which have had patient contact, viral hepatitis is commonly a potential risk. Other diseases which may be transmitted in like fashion are herpes, streptococcus, staphylococcus, tuberculosis, malaria and syphilis. In view of the potential seriousness of the diseases which might be contracted by post patient contact accidental needle sticks, hospitals and other institutions have found it necessary to engage in extensive testing and treatment in order to minimize the risk of the accident victim contracting a disease. After an accidental needle stick, it is typical to test for hepatitis by monitoring the patient for serum enzymes and viral antigens. Depending upon the circumstances, immune serum globulin may be administered.

Various types of needle shields including closures adapted for relative end-to-end insertion have been known. See generally, U.S. Pat. Nos. 3,537,452; 3,865,236; 4,419,098 and 4,438,845, as well as Swiss Pat. No. 448,389 and Italian Pat. No. 530,857.

In spite of these problems, attention has not been directed toward the same in the prior art and solutions to the same have not been forthcoming. U.S. Pat. Nos. 3,052,241 and 3,055,364 illustrate end insertion of a needle member into a medication containing vessel in order to facilitate transfer. An elongated slit member 32 is adapted to facilitate insertion of the needle member into the adjacent assembly without damage to the needle.

U.S. Pat. No. 4,356,822 discloses a syringe assembly wherein an outer tubular member is adapted to control the depth of needle penetration into a patient.

U.S. Pat. No. 2,857,912 discloses a construction of the prior art with the open end of the protector having resilient fingers to facilitate frictional engagement with the hub of the syringe. In one embodiment, the protector has hinged sections.

U.S. Pat. No. 2,997,043 discloses a strippable closure for a cannula point.

U.S. Pat. No. 2,854,976 is adapted to be employed with reusable syringes and provides a frictional hub engaging portion and a generally flat, open pedestal which provides an intermediate needle engaging support and a shield for the point region.

In spite of the foregoing, there remains a significant need for a closure member for a hypodermic needle which will effectively cover the needle, maintain sterility, if desired, and minimize the risk of accidental needle puncture wounds.

SUMMARY OF THE INVENTION

The above-described need has been met by the present invention. In the present invention, an elongated closure member, which is adapted to effectively seal the needle, is provided with a slot so as to permit relative lateral movement of the needle closure in effecting securement of the needle within the closure bore or removal of the closure from the needle. In addition, seal means may be provided so as to maintain desired sterility of the assembly. Also, mechanical hub engaging means, such as friction means, for example, may be provided to establish effective closure retention.

Means, which may be manually engaged, may be provided to permit manual indexing of the closure so as to orient the slot with the needle more readily. Also, pilot entry means may be provided to facilitate insertion of the needle into the closure board.

The closure is preferably substantially rigid and may advantageously be molded from a suitable plastic resinous material.

It is an object of the present invention to provide a hypodermic needle assembly which will effectively minimize hazards to medical personnel resulting from accidental needle punctures.

It is yet another object of the present invention to provide such an assembly which will be simple to use and economical to adopt.

It is another object of the present invention to provide such a needle assembly which may be employed while providing seal means to maintain sterility.

It is a further object of the present invention to provide for disposal of used hypodermic syringes in such fashion as to minimize risk to housekeeping personnel.

These and further objects of the present invention will be more fully understood from the following description of the invention on reference to the illustrations appended hereto.

DESCRIPTION OF THE PREFERRED EMBODIMENT

Figure 1:
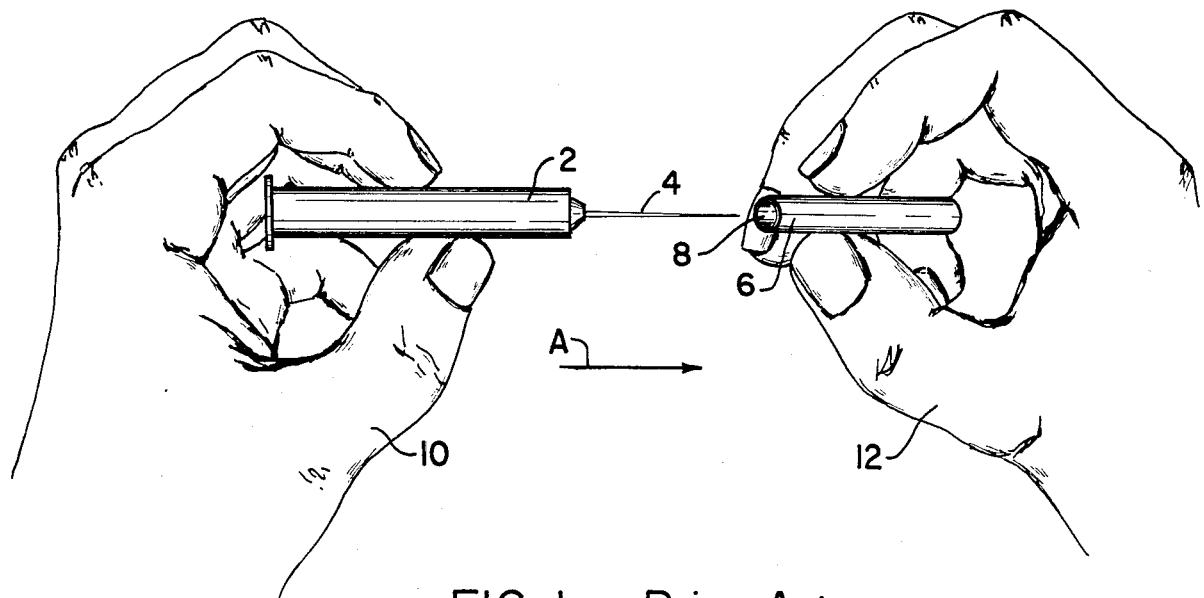
FIGS. 1 and 2 are partially schematic illustrations of the problem experienced with prior art devices.
Figure 2:
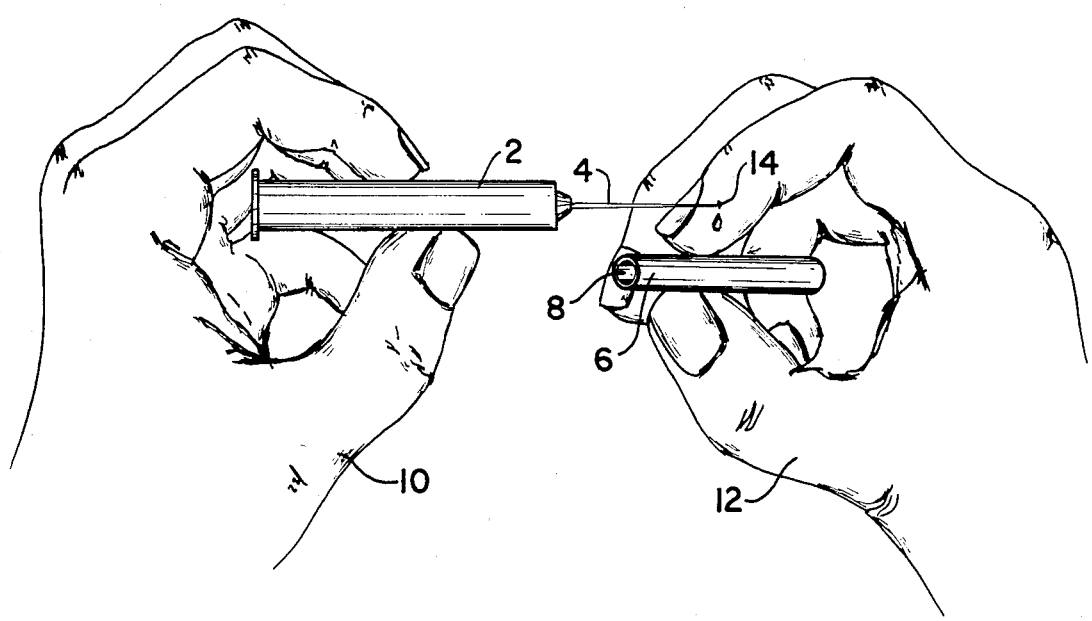

As is shown in FIG. 1, in effecting reclosure of a needle 4, by placing the prior art cap 6 over the needle 4, the end opening 8 of the cap provides access to the cap interior by the needle and necessitates relative closing movement in end-to-end fashion by a stabbing type motion. The syringe 2 is held in one hand 10, while the cap 6 is held in the other 12. While in general, one might think that this is a simple chore which could be accomplished without misadventure, statistics prove that misadventures occur all too frequently and result in a puncture wound 14 as shown in FIG. 2.

Figure 3:
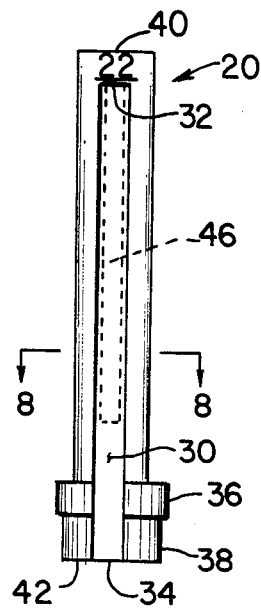
FIG. 3 is front elevational view of one form of closure member of the present invention.
Figure 4:
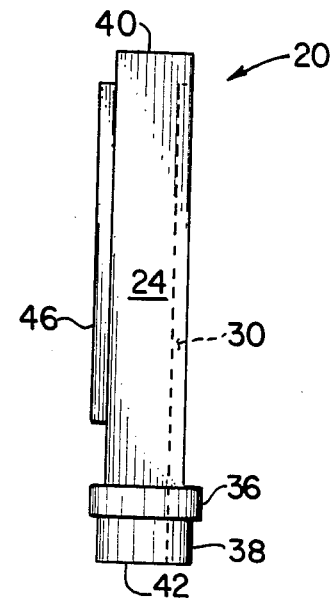
FIG. 4 is a right hand elevational view of the closure of FIG. 3.
Figure 5:
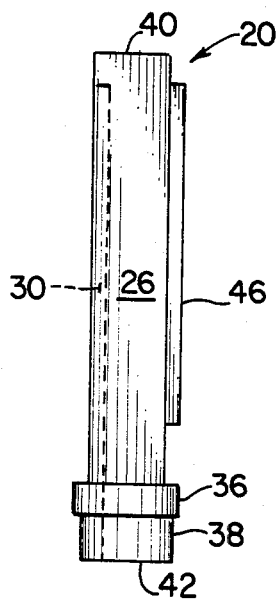
FIG. 5 is a left hand elevational view of the closure of FIG. 3.
Figure 6:
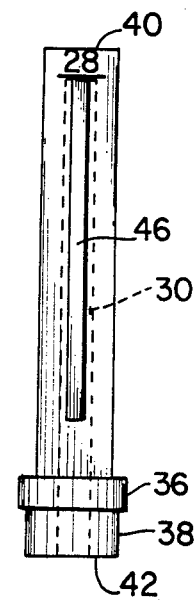
FIG. 6 is a rear elevational view of the closure of FIG. 3.
Figure 7:
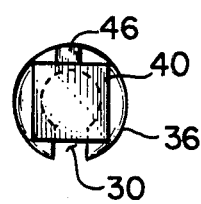
FIG. 7 is a top plan view of the closure of FIG. 3.
Figure 8:
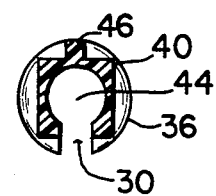
FIG. 8 is a cross-sectional illustration taken through 8—8 of FIG. 3 showing a portion of the closure wall.

As is illustrated in FIGS. 3–8, the system of the present invention contemplates use of an elongated closure 20 which is preferably composed of substantially rigid material and has an elongated slot 30 formed therein. The closure may be made from a suitable resinous plastic such as polypropylene or polystyrene, for example. The upper end 32 of the slot 30 is closed and the lower end 34 is open so as to provide the ability for lateral closing as will be discussed hereinafter. The closure, in the form shown, may be generally rectangular throughout its upper extremity and has a front wall 22, side walls 24, 26 and a rear wall 28. A radial enlargement 36 is provided adjacent to the lower end 42 of the closure and the portion 38 underlying the enlargement may be of generally cylindrical configuration and of enlarged dimension in order to facilitate engagement of the closure with the needle hub for retention purposes. The top 40 of the closure in the form shown is substantially rectangular. The upper end of slot 32, as is shown in FIG. 3, is in spaced relationship with respect to top 40 of the closure 20. The slot 30 is preferably of sufficient width to permit relatively easy insertion of the needle 4 into the closure and most preferably has a width less than about one-half the average external diameter of the closure. The slot 30 preferably has a length which is sufficient to facilitate relatively easy insertion of the needle 4 into the closure and interengagement with the needle hub.

Figure 9:
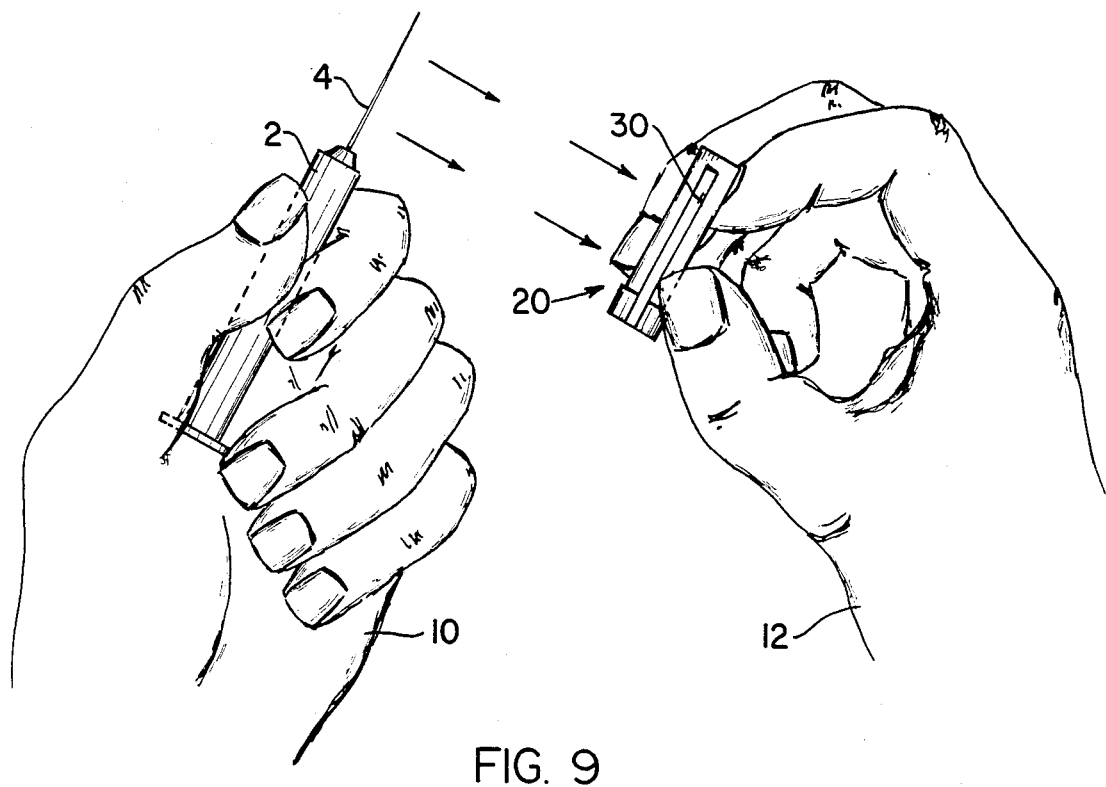
FIG. 9 is a schematic illustration showing movement involved in effecting assembly of the present invention.
Figure 10:
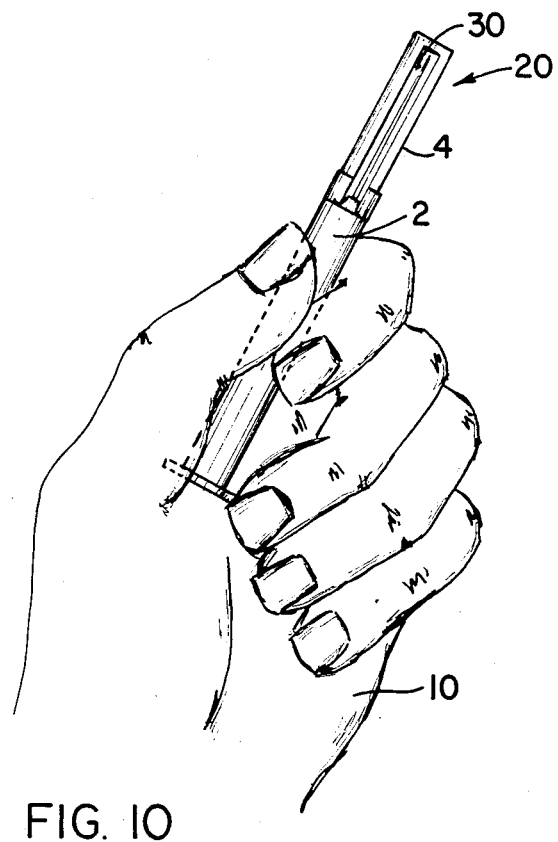
FIG. 10 is a schematic illustration showing the closure in position around the needle.

Referring to FIG. 9, in effecting protective covering of the needle 4 using the closure of the present invention, the slot 30 is positioned so as to face the needle 4. Relative lateral closing movement through movement of either or both members (in the direction indicated by the arrows) is employed to position the needle 4 within the bore of the closure and to permit the lower portion of the closure to effect mechanical interengagement with the needle hub. In FIG. 10, there is shown the completed assembly ready for disposal. If desired, additional protective means such as placing a further seal over the closure or placing the assembly within a disposable container may be employed.

In a preferred embodiment of the invention, means may be provided on the closure, preferably on the exterior, to permit manual engagement to determine in which direction the slot 30 is facing. In the form illustrated, in FIGS. 3 through 8, an elongated integrally formed rib 46 is positioned on rear wall 28. An individual using the closure upon feeling the rib 46 will know that the slot opening is on the opposite surface of the closure. It will be appreciated that in lieu of rib 46, various sorts of means in various positions may be employed to accomplish this objective. For example, a series of rib segments oriented in the direction illustrated, oriented horizontally or oriented diagonally may be positioned on one or more walls, as may other forms of irregularities such as dimples or detents or other depressions within the walls. Further, if desired, top wall 40 may be provided with an arrow pointing toward the slot opening. It will further be appreciated that the indicating means need not be purely means which could be manually noticed as in outward projections or recesses, but rather a color code could be provided with or without additional manually engageable means.

Figure 11:
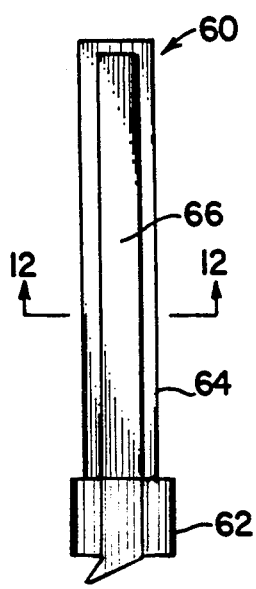
FIG. 11 is an elevational view of a form of hypodermic needle assembly of the present invention with a seal strip in place.
Figure 12:
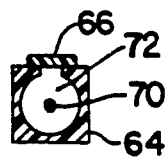
FIG. 12 is a cross-sectional illustration of the assembly of FIG. 11 taken through 12—12.
Figure 13:
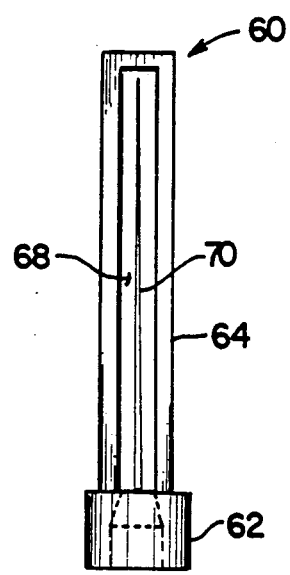
FIG. 13 is an elevational view of the assembly of FIG. 11 with the protective sealing strip removed.

Referring to FIGS. 11 through 13, there is shown a means of providing the hypodermic needle assembly of the present invention while providing for sterility. In the form illustrated, the closure 60 is provided with an enlarged lower portion 62, a reduced upper portion 64 and a removable sealing strip 66 which is adhesively bonded over the entire closure slot so as to maintain sterility of the needle. The tensile strength of the closure strip 66 is preferably greater than the adhesive bond to the closure 64 in order to facilitate removal of the strip 66 to permit access to the bore 68 within which the needle 70 is contained. If desired, the closure strip 66 may be provided with a pressure sensitive adhesive whereby the strip may be restored to the closure after use of the needle and repositioning the closure thereover. The closure may advantageously be composed of a flexible strip of a synthetic resin.

Figure 14:
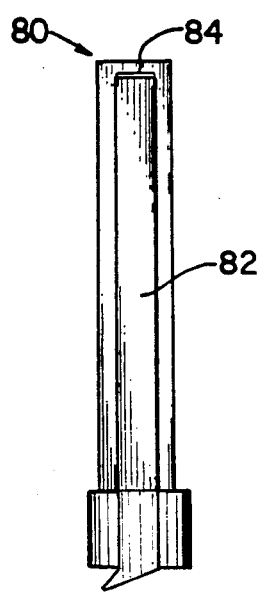
FIGS. 14 and 15 show modified forms of the invention wherein a protective sealing strip is hingedly secured to the closure.
Figure 15:
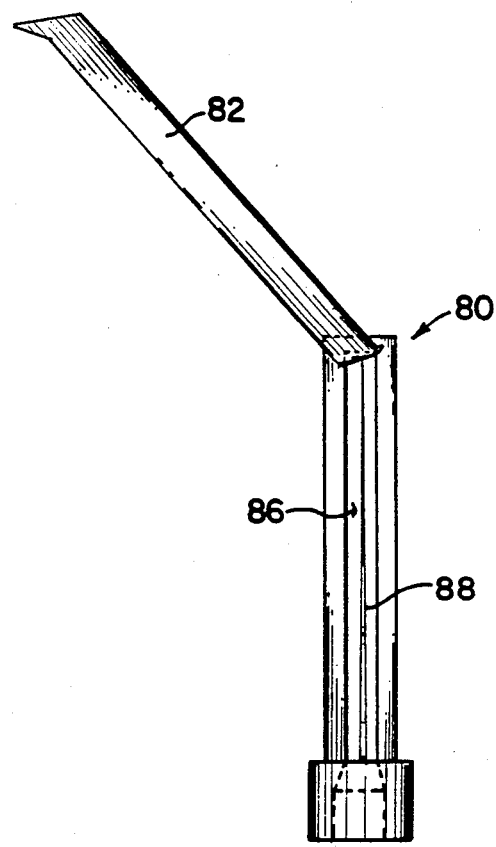

Referring to FIGS. 14 and 15, there is shown another embodiment of the invention wherein a closure 80 has a sealing strip 82 adhesively secured thereto in a fashion which will result in the strip 82 being permanently secured to the closure 80. In this embodiment, a hinge 84 which may be a tighter adhesive bond than that securing the remainder of the strip, an integrally molded connector or other suitable means is positioned so as to permit the rotation of the strip 82 with respect to the closure. The sealing strip may be integrally molded with the closure, if desired. Subsequent restoration of the strip after return of the needle 88 through the slot 86 may be provided, if desired.

Figure 16:
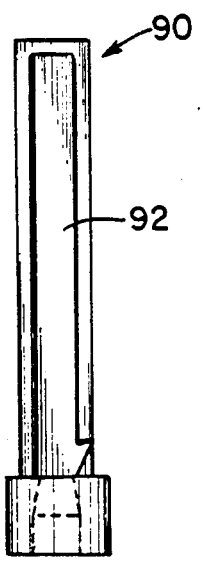
FIGS. 16 and 17 show a modified form of sealing arrangement of the present invention wherein the sealing strip is hingedly secured to the closure.
Figure 17:
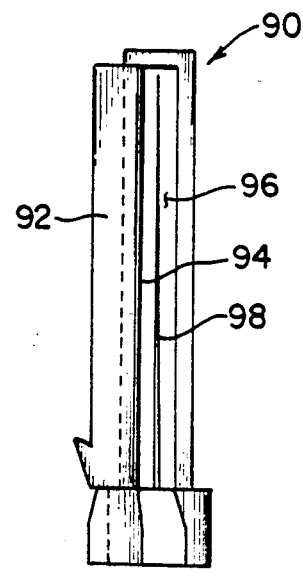

FIGS. 16 and 17 illustrate further modifications wherein the closure 90 is provided with a sealing strip 92 which is hingedly secured to the closure by means of hinge 94 which is generally vertically oriented. The slot 96 permits insertion of the needle 98.

Figure 18:
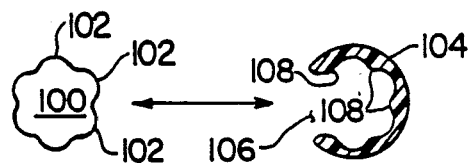
FIG. 18 is a partially schematic cross-sectional illustration showing hub engaging means and the associated needle hub.

Referring to FIG. 18, means for assisting with mechanical retention of the closure on the needle will be considered. A needle hub 100, which may be of the conventional variety is provided with an enlarged portion, which in the form shown has a plurality of radially outwardly projecting ribs 102. Within the lower portion of closure 104 which has slot 106, a plurality of radially inwardly projecting irregularities, which in the form shown, may be longitudinal rib segments 108. These closure segments are adapted to be intimately engaged within the regions between ribs 102 of the hub 100 through resilient yielding of the closure thereby permitting positioning of the closure over the needle and removal of the closure therefrom while resisting undesired removal.

Figure 19:
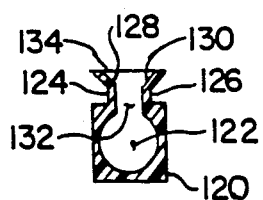
FIG. 19 is a cross-sectional illustration showing a form of pilot means adapted for use in the present invention.

Referring to FIG. 19, there is shown a closure 120 which defines a needle receiving bore 122 and has pilot means to facilitate introduction of the needle into the closure. A pair of wall segments 124, 126 connect a pair of diverging walls 128, 120 which define a pilot surface. In introducing a needle into bore 122, engagement by the needle with either pilot surface 128, 130 will serve to guide the same into throat 132 and ultimately into bore 122. The far end of the throat 132 has an end wall 134. This facilitates providing a suitable sealing strip for sterile conditions of the needle prior to use.

It will be appreciated, therefore, that the present invention provides a simple and efficient means of greatly minimizing the risk of undesired needle punctures with the attendant risk, discomfort and expense involved. All of this is accomplished in a manner which is simple to use and consistent with other desired medical objectives.

While for convenience of reference herein an elongated substantially rigid unitary molded closure composed of a plastic resinous material has been disclosed, it will be appreciated that other forms of closure materials and assemblies may be employed while obtaining the benefits of the present invention.

While for purposes of illustrations specific embodiments of the invention have been described above, it will be evident to those skilled in the art that numberous variations of the details may be made without departing from the invention as defined in the appended claims.

I claim:

1. A hypodermic needle assembly comprising
   a hypodermic needle,
   said needle having a tubular portion and a radially enlarged hub portion,
   elongated needle closure means for facilitating safe storage, transport and disposal of said needle,
   said closure being of generally tubular configuration having an open end generally adjacent said hub portion and a closed end,
   an elongated slot in said closure of predetermined generally fixed width and length and of sufficient size to permit relative lateral reinsertion of said needle into said closure,
   closure strip means secured to said closure over said slot,
   said closure strip means being in nonobstructing position with respect to said slot when in an open position,
   said slot originating in spaced relationship with respect to said closed end and extending to said open end, and
   said slot having a width less than about one-half the average external diameter of said closure, whereby relative lateral movement of said needle with respect to said closure will permit either reintroduction of said needle into said closure or removal of said needle therefrom, and engagement or disengagement of said enlarged hub portion by said closure.

2. The hypodermic needle assembly of claim 1 including
   a syringe barrel,
   said needle being secured to and in communication with said syringe barrel.

3. The hypodermic needle assembly of claim 2 including means on the interior of said closure for engaging said needle hub to resist undesired removal of said closure from said needle.

4. The hypodermic needle assembly of claim 3 including said closure strip being sealingly secured to said closure,
   whereby said needle will remain sterile prior to removal of said closure strip.

5. The hypodermic needle assembly of claim 4 including said closure strip being removably secured to said closure.

6. The hypodermic needle assembly of claim 4 including said closure strip being permanently secured to said closure, and
   said closure strip adapted to assume a first position covering said slot and a second position providing access to said slot.

7. The hypodermic needle assembly of claim 6 including said closure strip being hingedly secured to said closure.

8. The hypodermic needle assembly of claim 2 including position indicating means on said closure for providing means for indicating the position of said slot in order to facilitate the positioning of said closure on said needle.

9. The hypodermic needle assembly of claim 8 including said position indicating means having manually engageable means.

10. The hypodermic needle assembly of claim 9 including said position indicating means being outwardly projecting means formed integrally with said closure.

11. The hypodermic needle assembly of claim 10 including said closure being a unitary molded article.

12. The hypodermic needle assembly of claim 1 including pilot means for facilitating introduction of said needle into said closure through said slot.

13. The hypodermic needle assembly of claim 12 including said pilot means having a pair of laterally outwardly diverging portions.

14. The hypodermic needle assembly of claim 4 wherein said hub engaging means have a series of inwardly projecting members adopted to frictionally engage said needle hub.

15. The hypodermic needle assembly of claim 14 including said inwardly projecting means including rib members.

16. The hypodermic needle assembly of claim 2 wherein said needle is disposable.

17. The hypodermic needle assembly of claim 14 wherein said closure is composed of a substantially rigid material, and
said slot being of fixed dimensions.

18. A closure for a hypodermic needle having an enlarged hub portion comprising an elongated closure body of generally tubular configuration having an open end and a closed end,
an enlongated slot of predetermined generally fixed width and length in said closure of sufficient width and length to permit relative lateral reinsertion of said needle into said closure,
closure strip means secured to said closure over said slot,
said closure strip means being in nonobstructing position with respect to said slot when in an open position,
said slot originating in spaced relationship with respect to said closed end and extending to said open end,
said slot having a width less than about one-half the average external diameter of said closure,
means on said closure for engaging said enlarged hub portion of a said hypodermic needle, and
displaceable seal means for covering said slot, whereby relative lateral movement of said needle with respect to said closure will permit either reintroduction of said needle into said closure or removal of said needle therefrom, and engagement or disengagement of said enlarged hub portion by said closure.

19. The closure of claim 18 including
means on the interior of said closure for engaging a needle hub to resist undesired removal of said closure from the needle.

20. The closure of claim 19 including
said displaceable seal means having closure strip means being sealingly secured to said closure, whereby said needle will remain sterile prior to removal of said closure strip.

21. The closure of claim 20 including
said closure strip being removably secured to said closure.

22. The closure of claim 20 including
said closure strip being permanently secured to said closure, and
said closure strip adapted to assume a first position covering said slot and a second position providing access to said slot.

23. The closure of claim 22 including
said closure strip being hingedly secured to said closure.

24. The closure of claim 23 including
position indicating means on said closure for providing means for indicating the position of said slot in order to facilitate the positioning of said closure on said needle.

25. The closure of claim 24 including said position indicating means having manually engageable means.

26. The closure of claim 18 including laterally outwardly pilot means for facilitating introduction of said needle into said closure through said slot.

27. The closure of claim 19 including said hub engaging means include a series of inwardly projecting members adapted to frictionally engage the hub of said needle.

28. A hypodermic needle assembly comprising
a hypodermic needle,
said needle having a tubular portion and a radially enlarged hub portion
an elongated needle closure disposed in enclosing relationship with respect to said needle,
said closure being of generally tubular configuration having an open end generally adjacent said hub portion and a closed end, and
an elongated slot in said closure of sufficent width and length to permit relative lateral insertion of said needle into said closure,
closure strip means secured to said closure over said slot,
said closure strip means being in nonobstructing position with respect to said slot when in an open position,
said slot originating in spaced relationship with respect to said closed end and extending to said open end, and
said slot having a width less than about one-half the average external diameter of said closure, whereby relative lateral movement of said needle with respect to said closure will permit either introduction of said needle into said closure will permit either introduction of said needle into said closure or removal of said needle therefrom.

* * * * *

UNITED STATES PATENT AND TRADEMARK OFFICE
CERTIFICATE OF CORRECTION

PATENT NO. : 4,643,722

DATED : February 17, 1987

INVENTOR(S) : WILLIAM I. SMITH, JR.

It is certified that error appears in the above-identified patent and that said Letters Patent is hereby corrected as shown below:

On the Title Page, under ABSTRACT, line 4, "enlargement" should be --enlarged--.

Claim 28, column 8, lines 50-51, "will permit either introduction of said needle into said closure" should be deleted.

Signed and Sealed this

Twenty-fourth Day of November, 1987

Attest:

DONALD J. QUIGG

Attesting Officer

Commissioner of Patents and Trademarks